(12) United States Patent
Hanson

(10) Patent No.: US 6,585,749 B2
(45) Date of Patent: Jul. 1, 2003

(54) SURGICAL IMPLANT INSTRUMENT AND METHOD

(75) Inventor: David A. Hanson, St. Louis Park, MN (US)

(73) Assignee: Sulzer Spine-Tech Inc., Minneapolis, MN (US)

(*) Notice: Subject to any disclaimer, the term of this patent is extended or adjusted under 35 U.S.C. 154(b) by 0 days.

(21) Appl. No.: 09/920,153

(22) Filed: Aug. 1, 2001

(65) Prior Publication Data

US 2003/0028216 A1 Feb. 6, 2003

(51) Int. Cl.[7] ................................................. A61B 17/28
(52) U.S. Cl. ....................................... 606/208; 606/207
(58) Field of Search ............................... 606/151, 157, 606/122, 205–210, 139, 144

(56) References Cited

U.S. PATENT DOCUMENTS

| 4,877,020 A | | 10/1989 | Vich |
| 5,281,235 A | * | 1/1994 | Haber et al. ................. 606/139 |
| 5,443,514 A | | 8/1995 | Steffee |
| 5,522,899 A | | 6/1996 | Michelson |
| 5,609,636 A | | 3/1997 | Kohrs et al. |
| 5,669,909 A | | 9/1997 | Zdeblick et al. |
| 5,782,830 A | | 7/1998 | Farris |
| 5,797,909 A | | 8/1998 | Michelson |
| 5,888,222 A | | 3/1999 | Coates et al. |
| 5,989,289 A | | 11/1999 | Coates et al. |
| 6,033,438 A | | 3/2000 | Bianchi et al. |
| 6,066,174 A | | 5/2000 | Farris |
| 6,159,217 A | * | 12/2000 | Robie et al. ................. 606/207 |
| 6,174,311 B1 | | 1/2001 | Branch et al. |
| 6,203,544 B1 | | 3/2001 | Gotzen |
| 6,206,922 B1 | | 3/2001 | Zdeblick et al. |

FOREIGN PATENT DOCUMENTS

| WO | WO 98/17209 | 4/1998 |
| WO | WO 00/41654 A3 | 7/2000 |
| WO | WO 01/43620 A2 | 6/2001 |
| WO | WO 01/62191 A2 | 8/2001 |

* cited by examiner

Primary Examiner—Kevin T. Truong
(74) Attorney, Agent, or Firm—Merchant & Gould P.C.

(57) ABSTRACT

A surgical instrument suitable for use in an implant procedure is disclosed. A surgical instrument of the invention can be particularly advantageous for use in grasping, holding and placement of implants in an intervertebral disc space. In a typical embodiment, the surgical instrument has a grasping region to hold the implant, and an impact head for receiving a force in order to insert the implant.

21 Claims, 3 Drawing Sheets

SURGICAL IMPLANT INSTRUMENT AND METHOD

FIELD OF THE INVENTION

The present invention is directed to surgical instruments and procedures. In particular, the invention provides instruments and methods to facilitate surgical procedures involving grasping an implant or other item. In one embodiment, the invention is directed to an instrument that is particularly advantageous for holding an implant and facilitating placement of the implant between adjacent vertebrae.

BACKGROUND OF THE INVENTION

Surgical instruments and techniques are known for inserting implants at various locations in the body. One type of implant is the intervertebral implant, used to fuse opposing vertebral bodies.

Chronic neck and back problems can cause pain and disability for a large segment of the population. Frequently, the cause of the pain is traceable to diseased disc material between opposing vertebrae. When the disc material is diseased, the opposing vertebrae may be inadequately supported, resulting in persistent pain.

Surgical devices and techniques have been developed for removing diseased disc material and fusing the joint between opposing vertebral bodies. Stabilization and/or arthrodesis of the intervertebral joint can reduce the pain associated with a joint having diseased disc material. Some fusion techniques involve removal of the diseased disc, drilling a bore for receiving a fusion implant into the bore and inserting the implant between the opposing vertebral bodies.

Spinal fusion implants and related surgical instruments for implanting a fusion device are known and disclosed in, for example, U.S. Pat. Nos. 5,741,253; 5,658,337; 5,609,620; 5,145,732; 5,239,158; 5,239,157; 5,234,437; 5,458,638; 5,055,104; 5,013,373; 5,015,247; and 4,961,740, the disclosures of which are incorporated herein by reference.

Generally, the fusion device is implanted within a site prepared between opposing vertebrae. Typically, the site is a bore formed in the disk material that extends through the cortical end plates and into the cancellous bone of the opposing vertebrae.

Implants are generally constructed from a rigid, biocompatible material. Examples of such suitable materials include bone (e.g., autograft, allograft, artificial bone), ceramic, titanium, or stainless steel. Implants, especially intervertebral implants, often are designed to be used with specific insertion devices. The implants may be designed with features such as internal threading or grooves that mate with corresponding features on implant inserting devices. Thus, a different insertion device often is required for each type of implant used. Additionally, such devices often are complicated and time-consuming to use.

Accordingly, there is a continuing need for improved intervertebral stabilizing devices, methods, and instruments that reduce the time and steps needed to perform implantations, and provide increased structural integrity. The present invention addresses these needs.

SUMMARY OF THE INVENTION

The present invention provides instrumentation and methods to facilitate bone implantation. In particular, the invention provides an instrument including first and second arms pivotally connected, each arm having a handle. One of the arms has an impact head to receive placement forces and transfer them to the implant during placement. In one embodiment, the arms have locking members.

Preferably, the arms of the surgical instrument include a grasping region comprising an implant seat having a particular configuration. The grasping region is preferably configured to grasp an implant during placement.

In another aspect, the disclosure describes a method for inserting an implant. In one embodiment, the implant is placed in the implant seat of the surgical instrument and the arms are closed to capture the implant. The instrument and captured implant are placed at the insertion location and placement force is applied. The force is transferred from the impact head to the implant, thereby facilitating placement. The arms are opened and the instrument is removed.

DETAILED DESCRIPTION OF THE INVENTION

Throughout the specification, guidance may be provided through lists of examples. In each instance, the recited list serves only as a representative group. It is not meant, however, that the list is exclusive.

Throughout the specification unless otherwise stated, the terms "proximal" and "distal" are relative terms, the term "proximal" referring to a location toward the surgeon and the term "distal" referring to a location away from the surgeon. Thus, generally, when using an instrument of the invention for implantation procedures, the surgeon holds the proximal end and grasps an implant with the distal end of the instrument.

The invention is directed to surgical instruments and methods for grasping and positioning devices used in surgery such as surgical implants. In one embodiment, the invention is particularly useful for grasping and positioning an interbody spinal implant. As used herein, an "implant" includes any device that is inserted into the body of a human or animal patient. For exemplary purposes, the invention will be described with reference to an implant that facilitates fusion of adjacent vertebrae. Such an implant can be prepared from known implant materials including non-bone material such as titanium, stainless steel, porous titanium, ceramic, biopolymer such as polylactic acid (PLA) or polyglycolic acid (PGA), etc. or bone, including heterologous, homologous, autologous, artificial bone, etc. The implants can be threaded or non-threaded, grooved or non-grooved, or channeled or non-channeled. Examples of implants suitable for grasping and positioning with an instrument of the invention are disclosed in U.S. Pat. Nos. 5,609,636; 5,865,847; 5,947,971; 4,878,915; 4,877,020; 5,192,327; 4,501,269; 5,484,437; 5,593,409; 5,669,909; and 5,766,252, the entire disclosures of which are incorporated herein by reference.

DETAILED DESCRIPTION OF THE ILLUSTRATED EMBODIMENT

The invention will be described with reference to the accompanying drawings. The illustrated embodiment and description are for exemplary purposes to facilitate comprehension of the invention and should not be construed to limit the scope of the invention.

Figure 1:
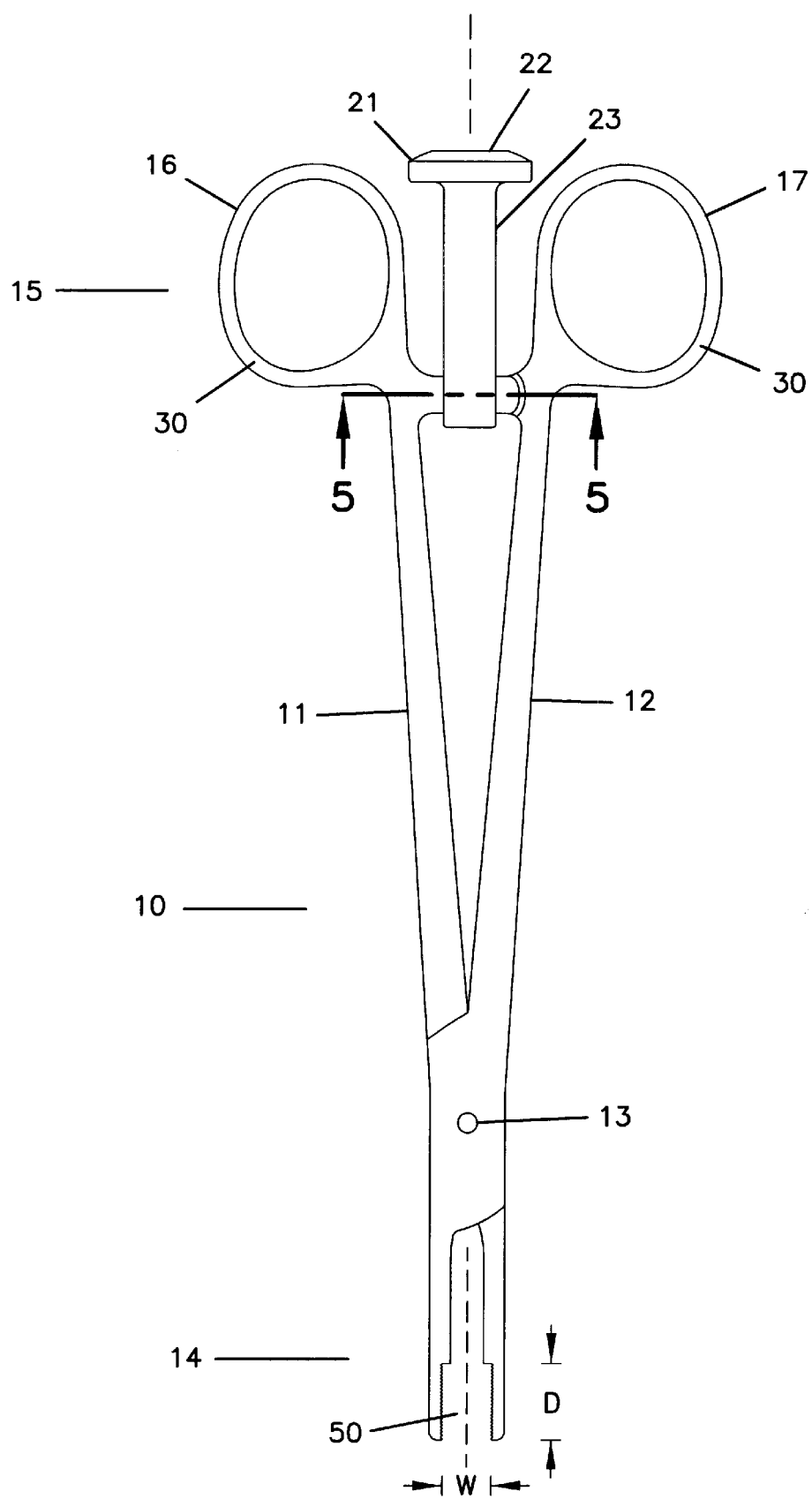
FIG. 1 is a top view of a surgical instrument according to the present invention in a closed position.

FIG. 1 is a top view of one embodiment of a surgical instrument 10 according to the invention, shown in a closed position. The surgical instrument 10 has first and second arms 11, 12. The first and second arms 11, 12 are interconnected at a pivot point 13 between the instrument's distal end 14 and proximal end 15. The arms 11, 12 may be interconnected by, for example, a hinge, pivot pin, rivet, screw or any other device or mechanism that allows for movement of the arms 11, 12 toward and away from each other. The arms 11, 12 have handles 16, 17 at the proximal end 15 of the surgical instrument 10. In one embodiment, the handles comprise finger and thumb receiving loops 30. Alternative handles include, for example, curved portions, formed grips, or other suitable gripping arrangements.

Figure 2:
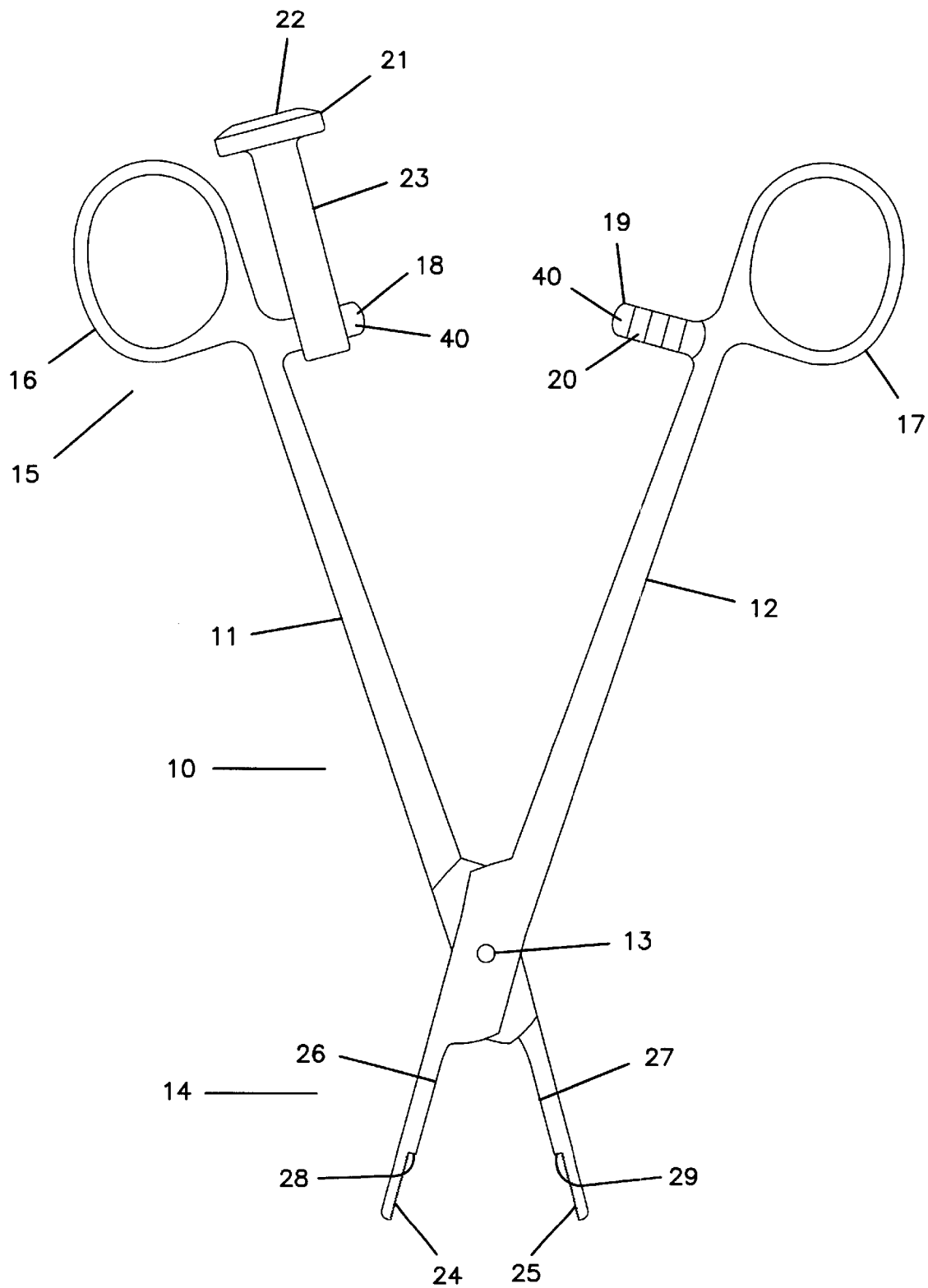
FIG. 2 is a top view of a surgical instrument according to the present invention in an open position.

FIG. 2 shows a top view of one embodiment of the surgical instrument 10 in an open position. In this embodiment, the instrument 10 has a locking arrangement including locking members 40, which function to incrementally, selectively, and reversibly adjust, set, or lock the first and second arms 11, 12 in a selected position. In other embodiments, an integrated locking arrangement may be omitted. In such an embodiment, the arms are maintained in a closed position to grasp the implant by, for example, exerting and maintaining a closing force on the arms by the surgeon's hand or via another instrument or other non-integrated locking arrangement.

In general, for instruments with locking members, the selected position in which the arms will be locked is a closed position, with the arms sufficiently close to grasp an implant. However, the locking members 40 allow the arms to be fixed in various selected positions. In one embodiment, the locking members 40 include, for example, projections attached to or integral with the arms or handles. The locking members may be located along any segment (distal, intermediate, or proximal) of the arms. Alternative integrated locking arrangements may include, for example, a retractable screw device, a notched member, a latching member, a sprocket wheel, a sliding member, or other adjustable locking mechanisms. Upon review of this disclosure, those of ordinary skill in the art may find it apparent to use other such arrangements to selectively adjust or relatively fix the position of the instrument's arm.

Figure 5:
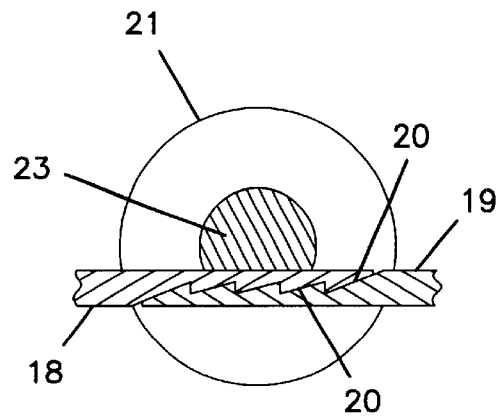
FIG. 5 is a cross-sectional view taken along lines 5—5 of FIG. 1.

The embodiment shown in FIG. 2 has locking members 40 in the form of first and second ratchet bosses 18, 19. The ratchet bosses 18, 19 extend toward each other from the first and second arms 11, 12. The ratchet bosses 18, 19 each comprise a series of ratchet teeth 20. The ratchet teeth 20 on one ratchet boss 18 are oriented to cooperate with corresponding and opposing ratchet teeth on the other ratchet boss 19. This configuration allows incremental or stepwise closure of the arms 11, 12 as the ratchet teeth 20 of the two ratchet bosses 18, 19 engage. FIG. 5 is a cross-sectional view taken through lines 5—5 of FIG. 1, showing the ratchet bosses 18, 19 and ratchet teeth 20 fully engaged. The ratchet bosses are disengaged to release the fixed relative position and open the arms by manipulating the handles in such a way as to separate the ratchet teeth.

The surgical instrument has an impact surface to receive a placement force. Placement force is the force used to place or insert an implant in its proper position. The force can result from manual tapping or impact blows, automatic tapping or impact from other devices, constant pressure (manual or automatic), or gradually varying pressures.

If the implant is incorrectly placed, for example too deep, the surgical instrument can be withdrawn while still gripping the implant. When manual removal of the instrument and implant is not possible or desired, a device such as a slap hammer can be used. In one embodiment, a slap hammer designed to fit over one or more arms 11, 12 of the instrument is used. Alternatively, a slap hammer designed to fit over a shaft 23 supporting an impact head 21, as shown in FIG. 1, can be used.

The impact surface accommodates the placement force, and may be attached to one or more handles and/or arms, one or both locking members, or a separate element designed specifically for receiving placement force. For example, in an embodiment having locking members protruding toward each other from the instrument arms, one or both of the locking members may act as the impact surface. One or both of the locking members or handles may be adapted to function as the impact surface for receiving the placement force. The adaptation may be in the form of an extended substantially flat surface, a reinforced area, or other suitable adaptation.

In the embodiment shown in FIGS. 1 and 2, the impact surface is an impact head 21. The impact head 21 is shown attached to or integral with one of the locking members 40. In an alternative embodiment, the impact head 21 may be attached to or integral with one of the handles 16, 17, or arms 11, 12. In a preferred embodiment, the instrument is configured such that when in a closed position, the placement force is directed substantially along a longitudinal axis of the instrument. This location provides for the placement force to be centered above the implant, which facilitates controlled placement of the implant.

In the embodiment shown in FIGS. 1 and 2, the impact head 21 is attached or formed in such a way that when the arms of the instrument are in a closed position, the impact head 21 is located centrally between the arms 11, 12, as shown in FIG. 1. As used herein, "closed position" refers to various positions in which the first and second arms 11, 12 have been brought towards each other sufficiently close to grasp an implant, and locking members, if present, are at least partially engaged. In the illustrated embodiment, the instrument is in a closed position when the arms 11, 12 are brought together and at least some of the ratchet teeth 20 are engaged. The variable locking means allows for various sized implants to be grasped with the instrument. The instrument shown in FIG. 1 is in a fully closed position with the arms 11, 12 brought together, all of the ratchet teeth 20 engaged and the ratchet bosses 18, 19 completely overlapping.

The illustrated impact head 21 comprises a receiving surface 22 joined to a shaft 23. The shaft 23 extends from one locking member 40, proximally along the longitudinal axis of the surgical instrument 10. FIG. 5 shows the impact head 21 centered on the shaft 23, and the shaft 23 positioned such that the impact head 21 is positioned substantially along a longitudinal axis of the instrument.

Figure 4:
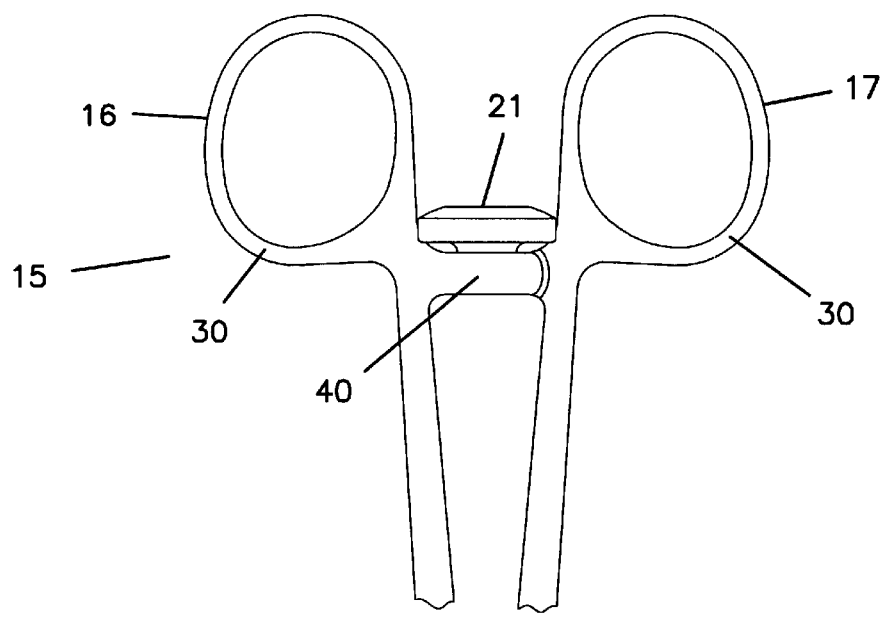
FIG. 4 is a partial top view of the proximal end of a surgical instrument according to the present invention in a closed position.

As shown in FIG. 2, the impact head 21 of the illustrated embodiment has a cross-sectional "T" shape. Other suitable impact head configurations may include, for example, columnar forms, square or rectangular forms, "I" shaped forms, button head forms, and other shapes or forms that one of ordinary skill in the art may find apparent to use as an arrangement to receive a placement force after reading this disclosure. In certain embodiments, the impact head 21 may: be at substantially the same level as the locking members 40, as shown in FIG. 4; extend beyond the proximal end of the handles 16, 17, as shown in FIGS. 1 and 2; be at any level in between these two points, such as at a point below the proximal end of the handles; or it may be distal to the locking members 40, provided adequate spacing between the handles exists to allow a mechanism for imparting placement force to engage the impact head.

Figure 3:
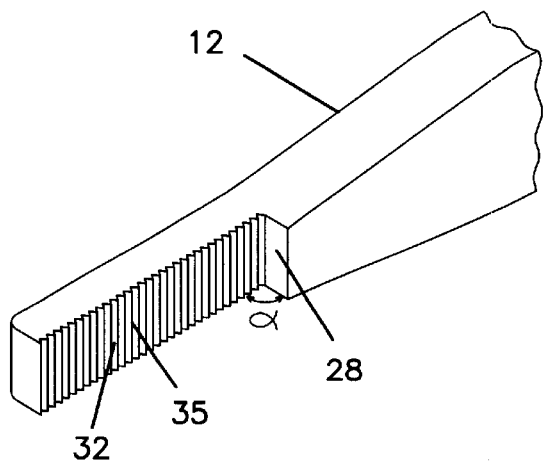
FIG. 3 is a perspective view of the distal end of one arm of a surgical instrument of the present invention.

The distal ends 14 of the arms 11, 12 form the grasping surface of the instrument. The interior surface of each arm in the grasping region is stepped from a first elevation 24, 25 at the extreme distal tip of the arm to a second elevation 26, 27 that projects toward a central longitudinal axis of the instrument. See FIG. 2. The step from the first elevation 24, 25 to the second elevation 26, 27 forms a shoulder 28, 29 on each arm. The area from the distal tips of the arms to the shoulders defines an implant seat 50. The interior surface of each arm at the first elevation comprises an engaging surface 32, as shown in FIG. 3.

The depth D of the implant seat 50 is the dimension from the distal tip of the arms to the shoulder. See FIG. 1. The width W of the seat is the dimension between the interior surfaces of the arms at the first elevation 24, 25 when the arms are in a fully closed position. The depth D and width W dimensions of the seat correspond to the height and width of an implant and can vary to suit a particular shaped and sized implant. The width W of the seat can be between about 2 mm and about 20 mm, generally about 6 mm to about 12 mm. The depth D is typically between about 4 mm and about 20 mm, more preferably about 6 mm to about 10 mm.

The implant seat 50 of the surgical instrument 10 formed by the interior surfaces 24, 25 and the shoulders 28, 29, is generally designed to fit the shape and size of a particular implant. For example, the grasping region of the instrument may include an internal channel shape so that a cylinder shaped implant grasped longitudinally "seats" fully within the instrument. In the illustrated embodiment, shoulders 28, 29 form an angle α that helps secure the implant in the instrument. See FIG. 3. In alternative embodiments, the shoulders can be rounded or sloped.

In one embodiment, the instrument has a locking mechanism that locks the arms together in various positions. In this embodiment, once an implant is grasped in the implant seat and the locking mechanism is engaged, the combination of the shoulders and locking mechanism secures the implant so that lateral compression is not solely necessary to hold and insert the implant. Lateral compression holds the implant in apposition to the shoulders so the placement force is directly and uniformly transferred to the implant. A suitable amount of lateral compression is that which is minimally sufficient to hold the implant in place.

The angle α between the first elevation 24, 25 and the second elevation 26, 27 may be from about 1 degree to about 179 degrees, but is generally from about 45 degrees to about 135 degrees. In the illustrated embodiment, the shoulders form an angle of approximately 90-degrees. The shoulders may have other geometric and angular configurations to accommodate varying shaped implants.

When the arms of the instrument are in a closed position, the interior surfaces of the arms at the grasping region are spaced apart, to accommodate the implant. In the embodiment shown in FIG. 1, the interior surfaces of the arms at the grasping region are substantially parallel at the first elevation when the arms of the instrument are in a fully closed position. This embodiment of the instrument is suitable for placing implants with substantially parallel outer edges. The interior surfaces of the arms and/or the shoulders at the grasping region may be curved or angled to accommodate different shaped implants. In any of the embodiments, the shoulders 28, 29 provide for secure gripping of the implant and for transferring the force placed on the impact head to the implant during placement.

FIG. 3 is a perspective view of the distal end of a single arm 12. Engaging surface 32 of the grasping region can be smooth or textured to provide a gripping surface. Examples of gripping surfaces include ridges 35, as illustrated in FIG. 3, grooves, textures, knurls or other treatments to improve the gripping characteristics of the implant seat.

The surgical instrument 10 may be provided in a kit that includes a selection of multiple instruments; each having incrementally sized and shaped implant seats suitable to accommodate varying implant configurations. Other seat configurations may become apparent to one of ordinary skill in the art, upon review of this disclosure, to accommodate implantation of pieces or devices having other varied widths, depths, and shapes.

In operation, a surgeon uses the surgical instrument 10 to selectively grasp and hold an implant within the implant seat. The surgeon incrementally adjusts and locks the instrument in a closed position by engaging the locking members. With the implant captured by the surgical instrument's implant seat, the surgeon places the implant adjacent the desired implantation location. The surgeon imparts a placement force upon the impact head 21 by tapping or applying pressure to the impact head. The force is transmitted along a longitudinal axis of the instrument to the implant to facilitate placement. The surgeon then manipulates the handles to disengage the locking members for removal of the instrument.

Situations may arise requiring complete or partial extraction of the implant after insertion, such as when the implant is inserted too deep. Manual force may not be sufficient to extract the instrument and implant. A slap hammer can be used to provide additional force to extract the instrument and implant. In one embodiment, a slap hammer is designed to fit over one or more arms 11, 12 of the instrument. The slap hammer is driven toward the proximal end 15 of the instrument. When the slap hammer strikes the handles 30, it imparts an extraction force along a longitudinal axis of the instrument. Alternatively, a slap hammer designed to fit over the shaft 23 supporting the impact head 21 can be used to extract the instrument and implant.

In view of its advantageous design, the surgical instrument facilitates implantation in at least two ways: first, by providing a device that securely captures a particularly sized and shaped implant, and second, by providing a device that transfers a force to an implant for proper placement.

From the foregoing detailed description and examples, it will be evident that modifications and variations can be made in the devices and methods of the invention without departing from the spirit or scope of the invention. Therefore, it is intended that all modifications and variations not departing from the spirit of the invention come within the scope of the claims appended hereto.

What is claimed is:

1. A surgical instrument comprising:
   a first and a second arm each having a proximal end and a distal end;
   a connector disposed between the proximal and distal end of each arm about which the first and second arms pivot;

a grasping surface located at the distal end of the first and the second arm, respectively; and an impact head attached to the instrument and configured to receive and transmit along a longitudinal axis of the instrument a force to an object releasably held at the grasping surface.

2. The surgical instrument of claim 1, wherein the distal end of the first and the second arm have exterior and interior surfaces, wherein the interior surfaces form a shoulder from a first elevation at the distal end to a second elevation projecting toward the longitudinal axis of the instrument; wherein the interior surfaces are spaced apart and substantially parallel when the instrument is in a fully closed position.

3. The surgical instrument according to claim 2 wherein the interior surfaces of the first elevation of the arms at the grasping region comprise a gripping surface.

4. The surgical instrument according to claim 3 wherein the gripping surface comprises ridges.

5. The surgical instrument according to claim 2 wherein a measurement between the interior surfaces of the arms at the first elevation of the grasping region is no less than 2 mm when the first and second arms are in a closed position.

6. The surgical instrument of claim 1, further comprising a locking arrangement configured to lock the arms in a selected position.

7. The surgical instrument of claim 6 wherein the locking arrangement comprises first and second locking members attached to the first and second arms, respectively, which can engage one another and lock the arms in a selected position.

8. The surgical instrument of claim 7 wherein the impact head is attached to one of the locking members and extends proximally along the longitudinal axis of the instrument when the instrument is in a closed position.

9. The surgical instrument according to claim 7 wherein the first and second locking members extend inward from the first and second arms, respectively, such that when the arms are brought together, the locking members engage and lock the arms in a selected position.

10. The surgical instrument according to claim 9 wherein the locking members comprise ratchet bosses with ratchet teeth.

11. The surgical instrument according to claim 1 wherein the impact head extends proximally at least to the proximal end of the first and second arms.

12. The surgical instrument according to claim 1, further comprising a first and a second handle located at the proximal end of the first and second arm, respectively.

13. The surgical instrument according to claim 12 wherein the handles comprise finger loops.

14. A surgical instrument comprising:
a first and a second arm each having a proximal end and a distal end, the distal end of the first and the second arm having exterior and interior surfaces, wherein the interior surfaces form a shoulder from a first elevation at the distal end to a second elevation projecting toward a longitudinal axis of the instrument, wherein the interior surfaces are spaced apart and substantially parallel when the instrument is in a fully closed position;
a connector disposed between the proximal and distal end of each arm about which the first and second arms pivot;
a locking arrangement configured to lock the arms in a selected position;
a grasping surface located at the distal end of the first and the second arm, respectively; and an impact head attached to the instrument and configured to receive and transmit along a longitudinal axis of the instrument a force to an object releasably held at the grasping surface.

15. A surgical instrument comprising:
a first and a second arm each having a proximal end and a distal end, the distal end of the first and the second arm having exterior and interior surfaces, wherein the interior surfaces form a shoulder from a first elevation at the distal end to a second elevation projecting toward a longitudinal axis of the instrument, wherein the interior surfaces are spaced apart and substantially parallel when the instrument is in a fully closed position;
a connector disposed between the proximal and distal end of each arm about which the first and second arms pivot;
a locking arrangement configured to lock the arms in a selected position;
a grasping surface located at the distal end of the first and the second arm, respectively; and
an impact head coupled to the locking arrangement and configured to receive and transmit along a longitudinal axis of the instrument a force to an object releasably held at the grasping surface.

16. A surgical instrument comprising:
a first and a second arm each having a proximal end and a distal end;
a connector disposed between the proximal and distal end of each arm about which the first and second wins pivot;
a grasping surface located at the distal end of the first and the second arm, respectively; and
an impact head attached to the instrument and configured to receive and transmit along a longitudinal axis of the instrument a force to an object releasably held at the grasping surface, wherein the impact bead extends proximally beyond the proximal end of the first and second aims.

17. A surgical instrument comprising:
a first and a second arm each having a proximal end and a distal end;
a connector disposed between the proximal and distal end of each arm about which the first and second arms pivot;
a grasping surface located at the distal end of the first and the second arm, respectively; and
an impact head attached to the instrument and configured to receive and transmit along a longitudinal axis of the instrument a force to an object releasably held at the grasping surface, wherein the impact head extends proximally to a point below the proximal end of the first and second arms.

18. A surgical instrument comprising:
a first and a second arm each having a proximal end and a distal end, the distal end of the first and the second aim having exterior and interior surfaces, wherein the interior surfaces form a shoulder from a first elevation at the distal end to a second elevation projecting toward a longitudinal axis of the instrument, wherein the interior surfaces are spaced apart and substantially parallel when the instrument is in a fully closed position;
a connector disposed between the proximal and distal end of each arm about which the first and second arms pivot;

a locking arrangement configured to lock the arms in a selected position;

a grasping surface located at the distal end of the first and the second arm, respectively; and an impact head attached to the instrument and configured to receive and transmit along a longitudinal axis of the instrument a force to an object releasably held at the grasping surface, wherein the impact head extends proximally beyond the proximal end of the first and second anus.

19. A surgical instrument comprising:

a first and a second arm each having a proximal end and a distal end, the distal end of the first and the second arm having exterior and interior surfaces, wherein the interior surfaces form a shoulder from a first elevation at the distal end to a second elevation projecting toward a longitudinal axis of the instrument, wherein the interior surfaces are spaced apart and substantially parallel when the instrument is in a fully closed position;

a connector disposed between the proximal and distal end of each arm about which the first and second arms pivot;

a locking arrangement configured to lock the arms in a selected position;

a grasping surface located at the distal end of the first and the second arm, respectively; and an impact head attached to the instrument and configured to receive and transmit along a longitudinal axis of the instrument a force to an object releasably held at the grasping surface, wherein the impact head extends proximally to a point below the proximal end of the first and second arms.

20. A surgical instrument comprising:

a first and a second arm each having a proximal end and a distal end, the distal end of the first and the second arm having exterior and interior surfaces, wherein the interior surfaces form a shoulder from a first elevation at the distal end to a second elevation projecting toward a longitudinal axis of the instrument, wherein the interior surfaces are spaced apart and substantially parallel when the instrument is in a fully closed position;

a connector disposed between the proximal and distal end of each arm about which the first and second arms pivot;

a locking arrangement configured to lock the arms in a selected position;

a grasping surface located at the distal end of the first and the second arm, respectively; and an impact head coupled to the locking arrangement and configured to receive and transmit along a longitudinal axis of the instrument a force to an object releasably held at the grasping surface, wherein the impact head extends proximally beyond the proximal end of the first and second arms.

21. A surgical instrument comprising:

a first and a second arm each having a proximal end and a distal end, the distal end of the first and the second arm having exterior and interior surfaces, wherein the interior surfaces form a shoulder from a first elevation at the distal end to a second elevation projecting toward a longitudinal axis of the instrument, wherein the interior surfaces are spaced apart and substantially parallel wlien the instrument is in a fully closed position;

a connector disposed between the proximal and distal end of each arm about which the first and second arms pivot;

a locking arrangement configured to lock the arms in a selected position;

a grasping surface located at the distal end of the first and the second arm, respectively and an impact head coupled to the locking arrangement and configured to receive and transmit along a longitudinal axis of the instrument a force to an object releasably held at the grasping surface, wherein the impact head extends proximally to a point below the proximal end of the first and second arms.

\* \* \* \* \*

UNITED STATES PATENT AND TRADEMARK OFFICE
CERTIFICATE OF CORRECTION

PATENT NO.     : 6,585,749 B2
DATED          : July 1, 2003
INVENTOR(S)    : Hanson It is certified that error appears in the above-identified patent and that said Letters Patent is hereby corrected as shown below:

<u>Column 8,</u>
Line 30, "second wins" should read -- second arms --
Line 37, "bead extends" should read -- head extends --
Line 39, "second aims" should read -- second arms --
Line 57, "aim having" should read -- arm having --

<u>Column 9,</u>
Line 10, "second anus" should read -- second arms --

<u>Column 10,</u>
Line 22, "wlien the" should read -- when the --
Line 30, "respectively and" should read -- respectively; and --

Signed and Sealed this

Thirtieth Day of December, 2003

JAMES E. ROGAN
*Director of the United States Patent and Trademark Office*